United States Patent
Metzger (10) Patent No.: US 6,905,513 B1
(45) Date of Patent: Jun. 14, 2005

(54) KNEE PROSTHESIS WITH GRAFT LIGAMENTS

(75) Inventor: Robert Metzger, Walkarusa, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 10/231,747

(22) Filed: Aug. 30, 2002

(51) Int. Cl.[7] .................................................. A61F 2/38

(52) U.S. Cl. .............................. 623/20.17; 623/20.14; 623/20.21

(58) Field of Search ........................ 623/20.14, 20.17, 623/20.21

(56) References Cited

U.S. PATENT DOCUMENTS

| | | | |
|---|---|---|---|
| 4,597,766 A | 7/1986 | Hilal et al. | |
| 4,770,663 A | 9/1988 | Hanslik et al. | |
| 4,773,910 A | 9/1988 | Chen et al. | |
| 5,067,962 A | 11/1991 | Campbell et al. | |
| 5,282,867 A | 2/1994 | Mikhail | |
| 6,004,351 A | 12/1999 | Tomita et al. | |
| 6,004,352 A | 12/1999 | Buni | |
| 6,203,576 B1 * | 3/2001 | Afriat et al. | 623/20.27 |
| 6,592,622 B1 | 7/2003 | Ferguson | |

FOREIGN PATENT DOCUMENTS

| | | | |
|---|---|---|---|
| FR | 2634373 | 7/1988 | |
| FR | 2663837 | 6/1990 | |
| FR | 2663837 A1 * | 1/1992 | ............. A61F 2/08 |
| FR | 2 734 709 A1 | 12/1996 | |
| GB | 2129306 A | 5/1984 | |

* cited by examiner

Primary Examiner—Cary E. O'Connor
Assistant Examiner—Candice C. Stokes
(74) Attorney, Agent, or Firm—Harness, Dickey & Pierce, P.L.C.

(57) ABSTRACT

The invention relates to a knee joint prosthesis having a bearing and a biologic ligament for replacing the articulating knee portion of a femur and a tibia. The knee joint prosthesis includes a femoral component, a tibial component, a bearing member, and a biologic ligament. The femoral component includes a first femoral bearing surface and a second femoral bearing surface. The tibial component includes a tibial bearing surface. The bearing member includes a first bearing surface which is operable to articulate with the first femoral bearing surface, a second bearing surface which is operable to articulate with the second femoral bearing surface and a third bearing surface which is operable to articulate with the tibial bearing surface. The biologic ligament is coupled to both the tibia and the femur to prevent the knee joint from dislocating and guiding the femoral component along a desired path during extension and flexion.

36 Claims, 8 Drawing Sheets

KNEE PROSTHESIS WITH GRAFT LIGAMENTS

TECHNICAL FIELD

This invention relates generally to a knee joint prosthesis which replaces the articulating knee portion of the femur and tibia, and more particularly, to a knee joint prosthesis having a biologically reconstructed ligament.

BACKGROUND

Motion of a natural knee is kinematically complex. During a relatively broad range of flexion and extension, the articulating or bearing surfaces of a natural knee experience axial rotation, adduction, abduction, translation in the sagittal plane (rollback and sliding), and translation in the coronal plane. Knee joint prostheses, in combination with ligaments and muscles, attempt to duplicate this natural knee motion, as well as absorb and control forces generated during the range of flexion.

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating the articulating motion of an anatomical knee joint.

There are known several types of knee prosthetics which are generally separated into two categories, first, regarding the amount of constraint or articulation allowed in the knee prosthetic joint. The types of knee prosthetics regarding constraint amount are cruciate retaining, posterior stabilized, and fully constrained. The cruciate retaining generally replaces only the articulating portions of the femur and the tibia when the soft tissue surrounding the knee can be saved or is not damaged. A posterior stabilized knee prosthetic is generally used when the posterior cruciate ligament needs to be resected due to damage or injury. Finally, the fully constrained knee prosthetic is used when almost all the soft tissue surrounding the knee needs to be resected or is no longer strong enough to perform the functions of the natural knee. Therefore, the cruciate retaining allows substantially all natural and uninjured motion of the knee.

The second category, and usable in each of the types of knees described above, are three different hinge or bearing mechanisms. The bearing mechanisms include a floating bearing, fixed bearing, and a hinge. The floating bearing is a bearing or meniscus replacement which is not affixed in any way to either the femoral component or the tibial component. It is simply a bearing between the femoral component and the tibial component and can move relative to either. This allows for greater muscle efficiency more closely simulating a natural knee. A fixed bearing, however, is fixed relative to the tibial component. Therefore, once the bearing is put in place, the femoral component rides on the bearing but the bearing does not move relative the tibial component. Finally, the hinged knee allows simple hinge movement from an extended to a flexed position. It is generally known in the art that any constrained knee prosthetic can be used with any bearing portion.

Soft tissue replacements or grafts may be implanted when soft tissue in a knee is injured or damaged and non-functioning. Generally, the articulating portions of the knee are satisfactory while the soft tissue ligaments and tendons surrounding the knee have been damaged due to injury or other causes. Therefore, it is only necessary to replace these damaged tendons and other soft tissues, rather than replacing the articulating portions of the knee joint. This is desirable because the natural knee joint provides the greatest range of motion and muscle efficiency, as opposed to prosthetic knee joints to date.

Although it is possible to more easily augment or retain the medial and lateral collateral ligaments in the knee and implant a knee prosthesis, this is generally difficult. A generally known knee prosthesis may possibly be used while including augmentation or implantation of medial and lateral collateral ligaments because these ligaments do not intersect the knee prosthetic. Therefore, a physician may be able to augment, such as tighten the medial or lateral ligaments, while also implanting a knee prosthetic.

It is not known, however, to provide a knee prosthetic, of any of the kinds commonly known, which can also be used with a soft tissue replacement procedure of the anterior cruciate or posterior cruciate ligaments. Rather, the art has proceeded in two divergent paths: one saving or resecting the soft tissue and choosing an appropriate knee prosthetic or two, simply replacing the soft tissue surrounding the knees. This reduces the choices to surgeons. Rather than allowing them to replace a damaged soft tissue portion with a graft and thereby needing a less constrained knee prosthetic. This is because knee prosthetics generally do not include clearances for soft tissue grafts that must intersect the articulating region of the knee.

Therefore, what is needed, is a knee prosthetic which can be used in conjunction with soft tissue replacement procedures to allow for greater abilities of surgeons to more closely replicate the natural knee with prosthetics. In particular, soft tissue replacements, such as anterior cruciate or posterior cruciate ligament replacements, are desirable to be used in a total knee replacement to provide for a more natural knee movement. Therefore, the physician would not need to choose to either attempt to save the soft tissue or replace it with a more constrained knee. The physician could resect all the soft tissue and then choose a more appropriate implant and replace the resected ligaments. In addition, using the soft tissue replacement techniques increases the ability of the prosthetic knee to more closely mimic the natural knee.

SUMMARY OF THE DISCLOSURE

The knee joint prosthesis allows for a graft for replacing the articulating knee portion of a femur and a tibia. The knee joint prosthesis includes a femoral component, a tibial component, a bearing member, and a graft. The femoral component includes a first femoral bearing surface and a second femoral bearing surface. The tibial component includes a tibial bearing surface. The bearing member includes a first bearing surface which is operable to articulate with the first femoral bearing surface, a second bearing surface which is operable to articulate with the second femoral bearing surface. The bearing may also include a third bearing surface which is operable to articulate with the tibial bearing surface. The graft is coupled to both the tibia and the femur to prevent the knee joint from dislocating and guiding the femoral component along a desired path during extension and flexion.

The femoral, tibial and bearing components may be precisely placed in the knee during implantation to provide a specific and precise final knee geometry and range of motion. Moreover, precise instrumentation may assist in this placement. Moreover, a single knee replacement surgery may be used to replace the soft tissues and the articulating knee components rather than providing for separate and distinct procedures.

In one embodiment, a knee joint prosthesis for replacing the articulating portion of a femur and a tibia is disclosed. The knee joint prosthesis includes a femoral component having a femoral bearing surface adapted to be secured to the distal end of the femur and a tibial component having a tibial bearing surface to be secured to the proximal end of the tibia. A bearing member having a first and a second bearing surface is provided to articulate with the femoral bearing surface and the tibial bearing surface. A transplanted biologic ligament connects the femur to the tibia and controls movement of the femur relative to the tibia.

A second embodiment of the knee joint prosthesis for replacing the articulating portion of a femur and a tibia, wherein a graft is also provided to interconnect the tibia and the femur. A femoral component may be secured to the distal end of the femur where the femoral component includes a first femoral bearing surface and a second femoral bearing surface. A tibial component is included which is adapted to be secured to the proximal end of the tibia where the tibial component includes a tibial bearing surface defining a tibial clearance. A bearing member defines a bearing clearance and includes a first bearing surface operable to articulate with the first femoral bearing surface and a second bearing surface operable to articulate with the second femoral bearing surface. The graft is has a first portion connected to a portion of the femur and a second portion connected to a portion of the tibia. The graft controls movement of the femoral component relative to the tibial component.

A third embodiment of a prosthetic knee joint to replace the articulating surface between a femur and a tibia includes a tibial component with a tibial tray defining a tibial tray bearing surface and a tibial clearance. The prosthetic knee also includes a bearing component that provides a tibial bearing surface and defines a bearing clearance. A graft operably interconnects the femur and the tibia through the tibial clearance and the bearing clearance.

A method of replacing the biological articulating knee portion of a femur and a tibia includes resecting an end portion of the tibia and femur. A tibial prosthetic component is then attached to the resected end portion of the tibia, the tibial prosthetic component has a bearing surface. A femoral prosthetic component is also attached to the resected end portion of the femur, the femoral prosthetic component also has a bearing surface. A bearing member is installed between the tibial prosthetic component and the femoral prosthetic component, the bearing member has a first surface to articulate with the femoral bearing surface and a second bearing surface to articulate from the tibial bearing surface. A graft to is prepared to connect the tibia and the femur and is then implanted to interconnect the tibia and the femur.

A second method of providing the knee prosthetic includes replacing the articulating knee portion of a femur and a tibia by resecting an end portion of the tibia and the femur. A tibial prosthetic component is attached to the resected end portion of the tibia, the tibial prosthetic component has a bearing surface and a tibial clearance. A femoral prosthetic component is attached to the resected end portion of the femur, the femoral prosthetic component has a bearing surface. A bearing member is installed between the tibial prosthetic component and the femoral prosthetic component, the bearing member has a bearing clearance and a first surface to articulate with the femoral bearing surface and a second bearing surface to articulate with the tibial bearing surface. A graft is prepared and implanted to interconnect the tibia and the femur.

The use of the present invention provides a knee joint prosthesis with a transplanted biologic ligament. The transplanted biologic ligament decreases the friction and wear on the prosthesis and thus provides increased durability and longevity. As a result, a knee prosthetic according to the present invention provides these and other advantages.

Further areas of applicability will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE EMBODIMENTS

The following description of the preferred embodiments concerning a floating bearing and a posterior stabilized fixed bearing knee joint replacement with a transplanted biologic ligament are merely exemplary and are not intended to limit the invention or its application or uses. It will be understood that the present invention may be practiced with any knee prosthetic to attach a graft between the femur and the tibia. That is, the procedure and invention of using a graft with a prosthetic knee joint may be used with any prosthetic knee joint such as a fixed bearing or floating bearing with a cruciate retaining knee. Moreover, the biological ligament may be any biological ligament or synthetic ligament that simulates a biological ligament.

Figure 1:
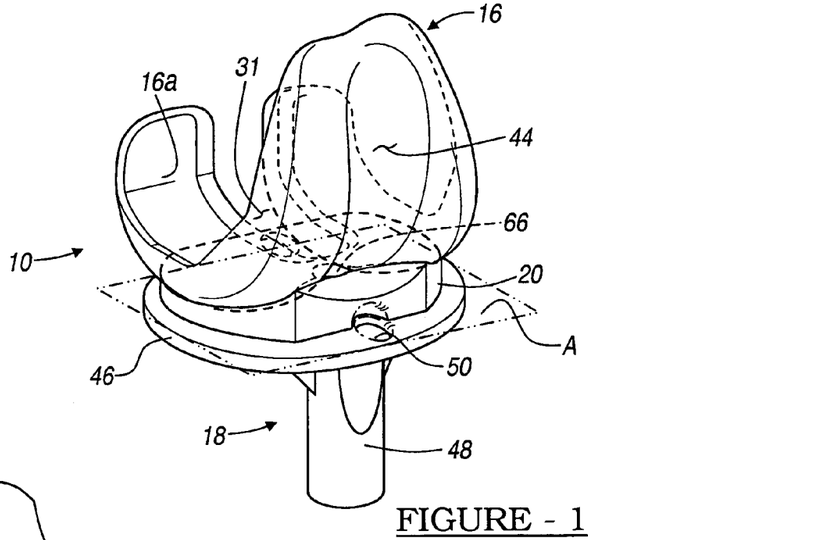
FIG. 1 is a perspective view of a floating bearing knee joint prosthesis according to a first embodiment.
Figure 2:
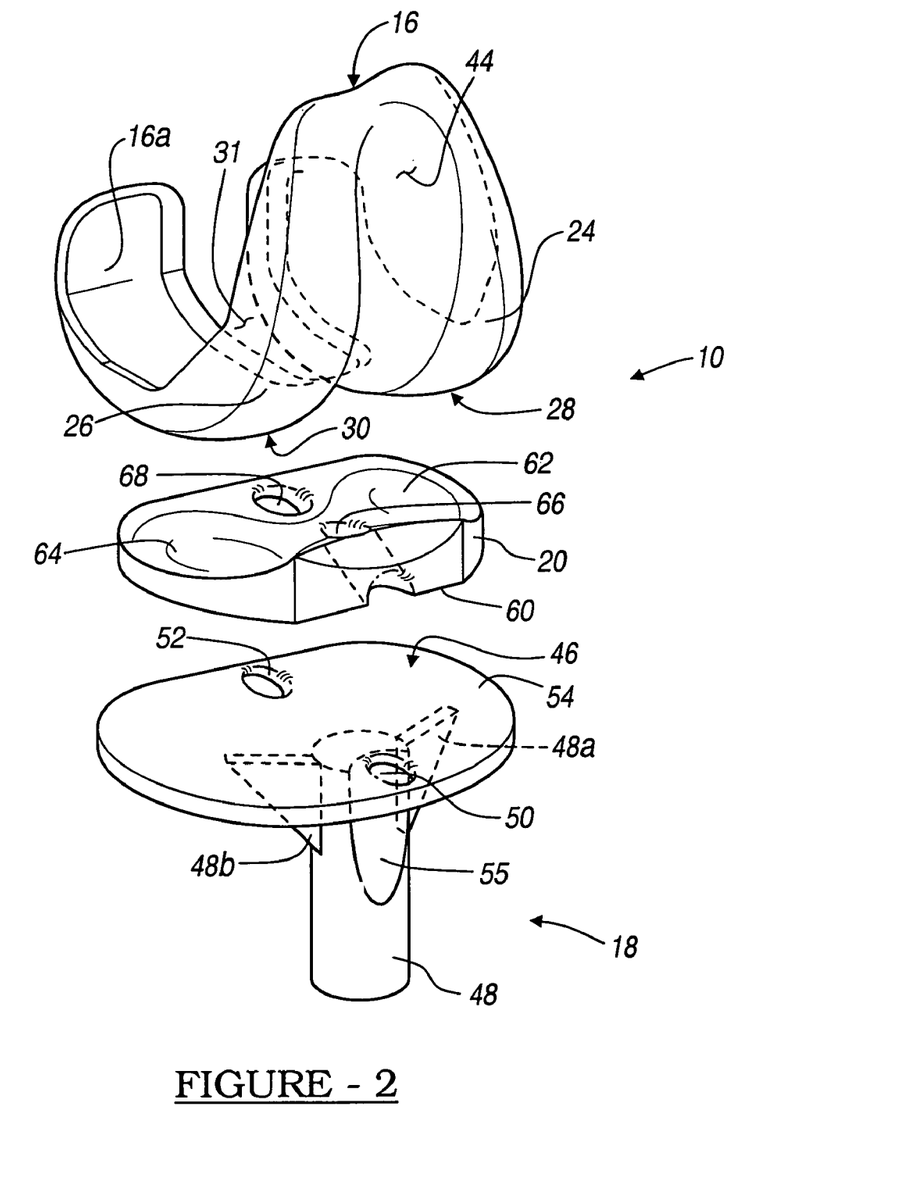
FIG. 2 is an exploded perspective view of the knee joint prosthesis of FIG. 1.

Referring to FIGS. 1–2, a cruciate retaining floating bearing knee joint prosthesis or knee prosthetic 10 is shown in accordance with the teachings of the present invention. The knee prosthetic 10 is designed to be used when a graft to replace either the posterior cruciate ligament (PCL) or the anterior cruciate ligament (ACL) is to be implanted. It is appreciated that the present invention may be utilized in knee replacements where other ligaments or other soft tissues that support the knee joint are also resected or replaced. It will be understood that a suitable right or left knee may be constructed. The knee prosthetic 10 includes a femoral component 16, a tibial component 18, and a floating bearing 20.

The femoral component 16 is adapted to be secured to a distal end of the femur 14 and includes a first condylar portion or condyle 24 and a second condylar portion or condyle 26 that provide a first bearing surface 28 and a second bearing surface 30, respectively. A femoral clearance 31 is defined between the first condyle 24 and the second condyle 26. The femoral component 16 further includes an arcuate patellar portion or patellar groove 44 which is disposed on the anterior portion of the femoral component 16. The patellar groove 44 is shaped to allow anatomical tracking of a natural or prosthetic patella. The patella prostheses which are compatible with the present invention may be of varying shape, such as round or domed shaped and may be constructed from polyethylene, polyethylene with metal backing or other suitable materials. The femoral component 16 is preferably formed as a unitary structure and preferably cast of a biocompatible high strength alloy such as cobalt-chromium-molybdenum alloy or other suitable material. All surfaces which do not contact the femur 14 are preferably highly polished to provide smooth articulating bearing surfaces. The femur contact surface 16a may be roughened or uneven to allow bone ingrowth or attachment with bone cement.

The tibial component 18 is adapted to be secured to the proximal end of the tibia 12 after the tibia 12 has been resected in a manner known in the art. The tibial component 18 includes a substantially planar platform-like tibial tray 46, an inferiorly extending tibial stem 48. The tibial stem 48 may also include stem fins 48a and 48b to stabilize the tibial tray 46 and to resist rotation of the tibial component 18. It is understood that other appropriate shapes of the stem 48, such as an I-beam cross-section may also be used. The tibial stem 48 is adapted to be received in a corresponding opening or bore made by a surgeon extending longitudinally in the center of the tibia 12. The tibial tray 46 also includes a first or anterior tibial passage or clearance 50 and a second or posterior tibial passage or clearance 52. The clearances 52 and 54 are adapted to allow a portion of a graft 70 (described herein and illustrated in FIG. 3) that is inter-connected between the tibia 12 and the femur 14, to clear the tibial component 18. The tibial stem 48 may also include a stem clearance 55 to allow additional clearance for the tibial tunnel, described herein. The stem clearance 55 may be included on any portion of the stem 48. The tibial tray 46 and stem 48 are generally manufactured of cobalt-chromium-molybdenum alloy or other suitable biocompatible material. The top or superior surface of the tibial tray 46 is highly polished to provide a substantially smooth tibial bearing surface 54. The stem 48 and stem fins 48a and 48b may be roughened to allow bone ingrowth or for better attachment of bone cement.

The floating bearing 20 is placed between the femoral component 16 and the tibial component 18. The floating bearing 20 has a substantially planar inferior bearing surface 60 which slidably moves and articulates relative to the highly polished tibial bearing surface 54, further discussed herein. The floating bearing 20 further includes a first bearing surface 62 and a second bearing surface 64. The first bearing surface 62 and the second bearing surface 64 articulate with the first bearing surface 28 of the first condyle 24 and the second bearing surface 30 of the second condyle 26 of the femoral component 16 respectively. The floating bearing 20 is preferably formed from a surgical grade, low friction, and low wearing plastic, such as UHMWPE or other suitable material.

The bearing 20 also includes an anterior bearing passage or clearance 66 and a posterior bearing passage or clearance 68. The anterior bearing clearance 66 and posterior bearing clearance 68 are formed in the bearing component 20 so that the bearing component 20 may articulate with the tibial bearing surface 46 while still allowing clearance for the graft 70. That is, that the bearing component 20 may slide along the tibial bearing surface 46 without being constrained by the graft 70. As particularly shown in FIG. 2, the anterior passage 66, and the posterior clearance 68 are generally oval shaped so that the bearing component 20 may move anterior and posterior on the tibial bearing surface 46 as the femoral component moves from extension to flexion as described further herein. When assembled, as particularly shown in FIG. 1, the anterior tibial passage 50 is substantially aligned with the anterior bearing passage 66 when the knee prosthetic 10 is extended. Additionally, the posterior tibial passage 52 is substantially aligned with the posterior bearing passage 68 when the knee prosthetic 10 is extended. In this way, the graft 70 may pass between the respective anterior clearances 50, 66 and posterior clearances 52, 68.

Figure 3:
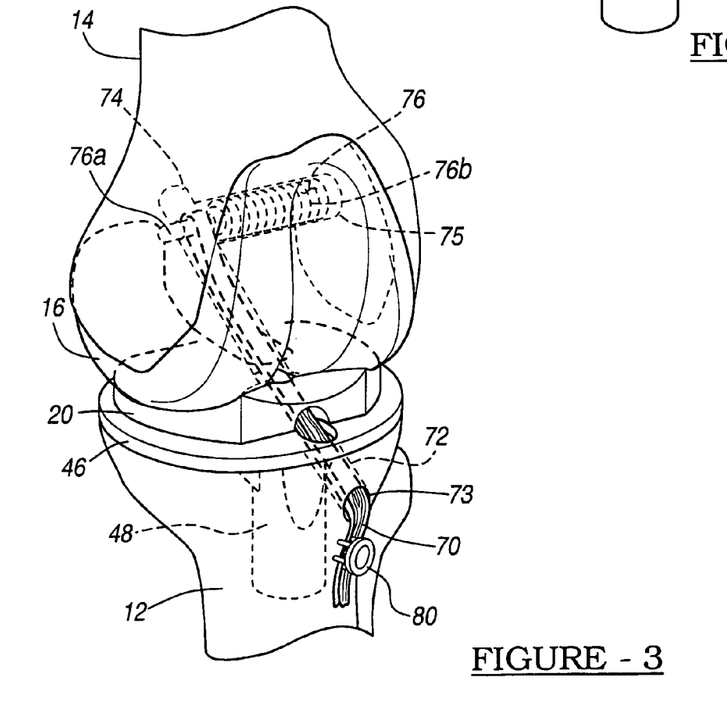
FIG. 3 is a perspective view of the floating bearing knee in FIG. 1 implanted.

With particular reference to FIG. 3, the knee prosthetic 10 is shown implanted into a knee joint. In particular, the femoral component 16 has been implanted onto the distal end of the femur 14. Furthermore, the tibial component 18 has been affixed to the proximal end of the tibia 12. The bearing 20 has been placed in between the tibial component 18 and the femoral component 16. The implanted knee prosthetic 10 defines an articulating plane or portion. A plane of articulation A is defined by the tibial bearing surface 46 of the tibial component 18. This is the plane along which the bearing 20 articulates. Additionally, an articulating region or area of the knee prosthetic 10 is defined generally having an inferior plane defined by the tibial bearing surface 46. A superior plane defined by the first and second bearing surfaces 28 and 30 of the femoral component 16. Finally the anterior, posterior, lateral, and medial sides of the articulating area are defined by the anterior, posterior, medial, and lateral edges of the femoral component 16 and the tibial component 18.

Also illustrated in FIG. 3 is the graft 70 illustrated as an ACL graft 70 herein. The ACL graft 70 can be implanted into the femur 14 using any generally known means and implants. The knee prosthetic 10 according to the present invention allows for the placement of a natural ACL, using generally known ACL replacement techniques, due to the anterior clearances 50, 66. In particular, the ACL graft 70 is allowed to extend through and from a tibial tunnel 72 to a femoral tunnel 74 because of the anterior tibial clearance 50 and the anterior bearing clearance 66. The ACL graft 70 is able to pass through the tibial articulating plane A and the knee prosthetic articulating region defined by the portions of the knee prosthetic 10. It is because of the anterior clearances 50, 66 that the ACL graft 70 is allowed to clear the articulating region of the knee prosthetic 10. The ACL graft 70 is then looped over a femoral fixation device 76 such as that disclosed in U.S. patent application Ser. No. 08/342,324 entitled, "Bonemulch Screw Assembly for Endosteal Fixation of Soft Tissue Grafts and Method for Using Same" and that disclosed in U.S. patent application Ser. No. 10/066,519 entitled, "Apparatus and Method for Manipulating a Flexible Strand and Soft Tissue Replacement During Surgery," both incorporated herein by reference. Then the ACL graft 70 is passed back out through the anterior clearances 50, 66 of the knee prosthetic 10 and is affixed to the tibia 12 using a tibial fixation device 80. The tibial fixation device 80 may be any appropriate tibial fixation device such as the device disclosed in U.S. patent application Ser. No. 09/616,544 entitled, "Apparatus and Method for Tibial Fixation of Soft Tissue," incorporated herein by reference.

The implantation of the ACL graft 70 allows a knee prosthetic to more closely simulate biological movements and increase longevity of the knee. Additionally, the ACL graft 70 may be a biological graft. This allows for a secure initial mechanical connection of the femur 14 and the tibia 12, using the ACL graft 70 and the femoral fixation device 76 and the tibial fixation device 80. Therefore, no other fixation means is necessary to reproduce the functioning of the ACL in a biological knee. Furthermore, using a biocompatible ACL graft 70 reduces the possibility of rejection and the overall longevity of the functioning of the ACL graft 70. In particular, the patients own tendons may be used to create the ACL graft 70.

Figure 4:
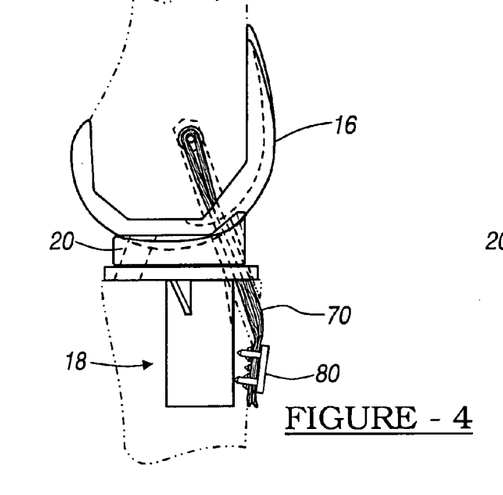
FIG. 4 is a sagittal elevational view of the knee joint prosthesis shown in FIG. 1 implanted into a knee and including an ACL replacement.
Figure 5:
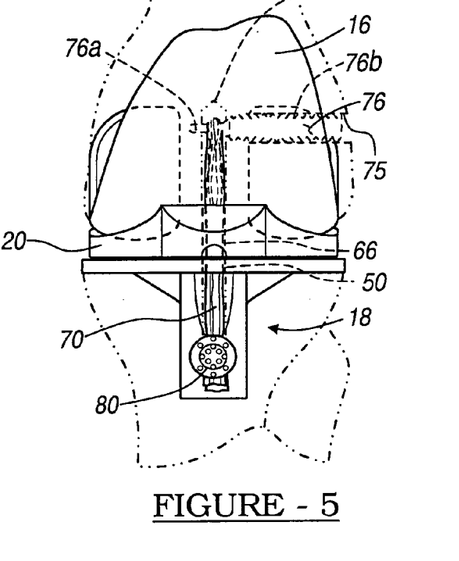
FIG. 5 is a coronal elevational view of the knee joint prosthesis shown in FIG. 1 implanted into a knee including an ACL replacement.

In the first use of the first embodiment illustrated in FIGS. 1–5, the ACL graft 70 is configured to replicate the function of the biological ACL. In this configuration the ACL graft 70 is connected to the tibia 12 and the femur 14 in a configuration as shown in FIGS. 3–5 and described above. The ACL graft 70 helps prevent posterior subluxation of the femur 14. A second use includes a PCL graft 90 interconnecting the tibia 12 and the femur 14. As the knee joint is moved from extension to flexion, particularly shown in FIGS. 10a–10e, the PCL graft 90 restrains the posterior movement of the tibia 12 with respect to the femur 14 and causes rollback.

Figure 6:
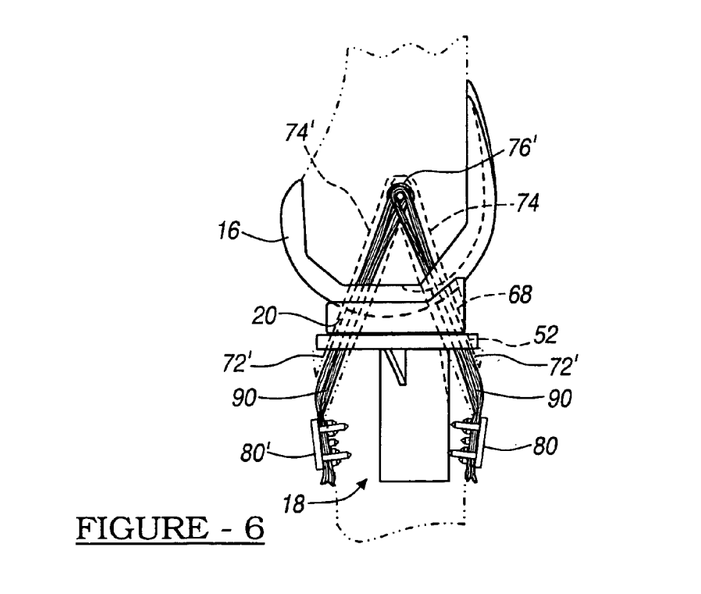
FIG. 6 is a sagittal elevational view of the knee joint prosthesis of FIG. 1; implanted into a knee including a PCL replacement.

With references to FIG. 6, a third use of the first embodiment of the knee prosthetic 10 is illustrated. The knee prosthetic 10 illustrated in FIG. 6 is substantially identical to the knee prosthetic 10 as described in relation to FIGS. 1–5. Illustrated in FIG. 6, is the knee prosthetic 10 including both the implantation of the ACL graft 70 and a posterior cruciate ligament (PCL) graft 90. It will be understood that the ACL graft 70 illustrated in FIGS. 1–5 is implanted to replace a natural ACL. The PCL graft 90, illustrated in FIG. 6, is a graft that replaces a PCL that has been resected or damaged in a natural knee. The PCL graft 90, however, is implanted substantially similarly to the ACL graft 70 described below. It will be understood that the appropriate angles and tensioning of the PCL graft 90 will necessarily differ from the same angles and tensioning of the ACL graft 70. It is also understood that the PCL graft 90 may be formed from the same or similar materials as the ACL graft 70.

The PCL graft extends through a posterior tibial tunnel 72' and a posterior femoral tunnel 74' that is formed in the femur 14. The PCL graft 90 is first placed through the posterior tibial tunnel 72' and then through the posterior tibial clearance 52. The PCL graft 90 is passed through the posterior bearing clearance 68. The PCL graft 90 is then placed through the posterior femoral tunnel 74' and affixed therein with a femoral fixation device 76'. The femoral fixation device 76', can be any appropriate femoral fixation device and may be identical to the femoral fixation device 76 illustrated in FIG. 3. After the PCL graft 90 has been placed over the femoral fixation device 76', both ends of the PCL graft 90 are then affixed to the tibia 12 using any appropriate tibial fixation device 80'. The tibial fixation device 80' may be identical to the tibial fixation device 80 illustrated in FIG. 3. It will be understood that the third use, illustrated in FIG. 6, will include the same features as the first use illustrated in FIGS. 1–5. Generally, those include that the posterior bearing clearance 68 allows for movement of the bearing 20 during flexion of the knee joint. Furthermore, the PCL graft 90 is harvested and implanted with substantially the same techniques and methods as described above, however creating a posterior tibial tunnel 72' and a posterior femoral tunnel 74'.

The knee prosthetic 10 allows for both a total knee replacement and a biological graft to replace either a resected ACL, PCL, or both. The ACL and PCL may need to be replaced when they are compromised or non-functioning. In this way, an immediate mechanical fixation of the knee may be produced without requiring the use of synthetic mechanical devices. In particular the grafts 70, 90 can be formed from the patient's own tissue into whom the knee prosthetic 10 is implanted. This substantially eliminates any complications regarding interactions between the implant and the patient. Furthermore, the grafts 70, 90 generally have greater longevity than known artificial components formed as a part of a knee prosthetic.

The knee prosthetic 10, including the ACL graft 70, of the present invention may be formed by any appropriate methodology. The following, while not meant to be an exhaustive explanation, describes the implantation of a knee prosthetic 10 and the ACL graft 70. Moreover, both the ACL graft 70 and the PCL graft 90 may be implanted. The methodology may also be used to perform a total knee replacement having a ligament performing the function of the PCL graft 90, with minor changes. Also, it is contemplated that the knee prosthetic 10, of the present invention, may be implanted using a variety of steps that are not found in the methodology, illustrated or described, but do not depart from the scope of the present invention.

Generally the method includes a complete resection of both the ACL and the PCL ligaments to allow for a total knee replacement and reconstruction with the ACL graft 70 and the PCL graft 90. Although the following description refers specifically to a total knee replacement including the ACL graft 70, it will be understood that a similar procedure may be followed to produce the required posterior tunnels for the PCL graft 90.

First, the proximal end of the tibia 12 is resected and shaped to correspond to the size and shape of the tibial component 18. Next, the distal end portion of the femur 14 is resected to and shaped to correspond to the size and shape of the femoral component 16. The tibia 12 and the femur 14 may be resected using various methods known in the art. For example, the tibia 12 or femur 14 may be resected using a bone saw, chisel or laser.

The internal physiology and geometry, specifically after resection may correspond to a specific tibial component and a specific femoral component such that a tibial and femoral tunnel produced using a particular trial components produce a predetermined constraint and roll back in the knee. A pretuned trial component allows a physician to predetermine the amount of rollback or constraint that will be produced in the knee after the knee prosthetic 10 has been implanted and the reconstruction of the ACL graft 70 and a PCL graft 90 are completed. This allows the physician to more closely understand the kinematics of the implanted knee so that a proper knee may be chosen for a particular patient. Therefore, a plurality of related trial components to produce the required tibial and femoral tunnels may be used in association with a specific plurality of knee implants so that a predetermined constraint and motion of the knee is known.

To ensure that enough, or particular, amount of rollback or constraint will be provided by the knee prosthesis the tunnels forming both the tibial tunnels 72, 72' and the femoral tunnels 74, 74' may be precisely formed and matched with a particular total knee prosthesis to produce the desired amounts of rollback and constraint. For example, with reference to FIG. 7, the anterior tibial tunnel 72 may be formed using a tibial trial component 91 and a tibial drill guide 92. A tibial trial stem 91a is fit into the bore formed in the tibia 12 to receive the tibial component 18. The tibial trial component 91, however, ensures that the proper tibial component 18 is chosen. The tibial trial stem 91a is exemplary illustrated in an I-beam configuration. It will be understood, that other stem configurations may be used. It will also be understood that the I-beam configuration may be used as the stem of the prosthetic tibial component. In addition to this, the tibial trial component 91 can also assist in guiding the tool or drill bit which forms the tibial tunnel 72. In particular, the tibial trial component 91 includes a tibial trial component tray 93 which includes an anterior guide bore 94 and a posterior guide bore 95.

Figure 7:
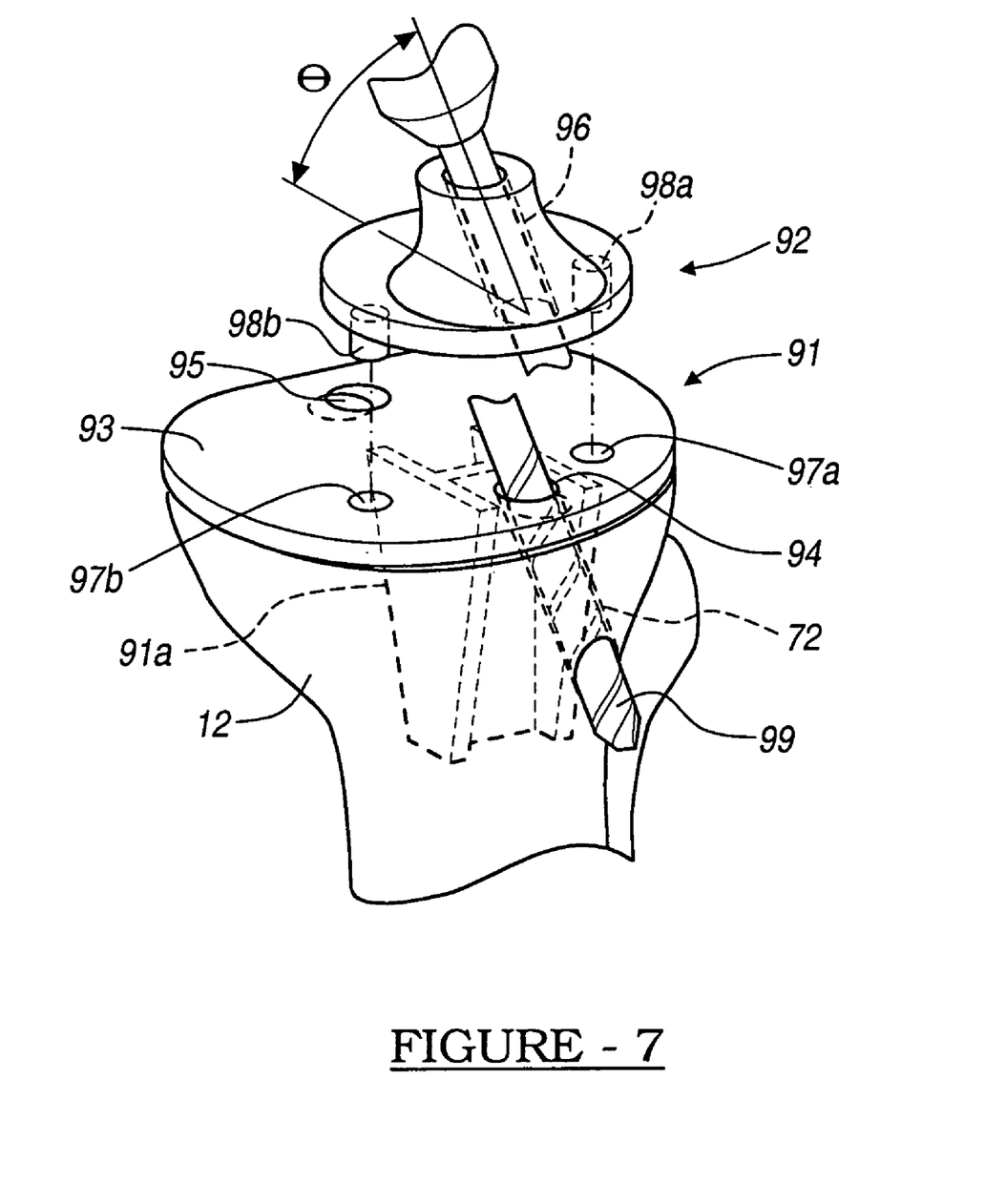
FIG. 7 is an exploded view of a tibial drill guide and tibial trial component used to create desired tibial tunnels.

The tibial tray 93 also receives the tibial drill guide 92 which includes a drill guide bore 96 and is coupled to the tibial tray 93. Although the tibial drill guide 92 may be received on the tibial tray 93 using any appropriate means to ensure that the drill guide does not move during the procedure, the tibial drill guide 92 is exemplary received on the tibial trial tray 93 in holding bores 97a and 97b which receive drill guide posts 98a and 98b. When the posts 98a, 98b are received in the bores 97a, 97b, the tibial drill guide 92 is substantially fixed to the tibial trial component 91. A plurality of distinct tibial drill guides 92 may be provided to form various and distinct tibial tunnels 72. The drill guide bore 96 includes an angle θ relative the tibial trial tray 93. The angle θ ensures that only a predetermined tibial tunnel 72 is formed. Various tibial drill guides 92 may include angles other than angle θ to provide various other tibial tunnel 72 variations.

The angle of the tibial tunnel 72 relative the tibial component and the femoral component determine the point at which rollback may occur. By varying these the time at which rollback begins may be changed and predetermined. Also positioning the tibial tunnels 72 at various degrees may control other constraints on the implanted prosthetic.

A drill bit 99 may then be inserted through the guide bore 96 and through the appropriate guide bore 94 or 95. If the anterior tibial tunnel 72 were being formed then the drill guide bore 96 is aligned with the anterior guide bore 94. This assists the physician in forming the appropriate tibial tunnel to receive the ACL graft 70 and to produce the desired constraint of the prosthetic knee. The appropriate tibial drill guide 92 may also be affixed to the bores 97a, 97b to aligned with the posterior guide bore 95 to form the posterior tibial tunnel. It will be further understood that varying knee prosthetics may use varying tibial tray trial components 91 and varying tibial drill guides 92 to produce the desired tibial tunnels.

Although not specifically illustrated, a tibial drill guide may also be keyed specifically to the bore that is formed in the tibia 12 to receive the tibial stem 48 of the tibial component 18. This eliminates the requirement of the tibial trial component 91 when forming the tibial tunnel.

In addition, a femoral drill guide may also be provided to form the femoral tunnels. The femoral drill guide may also be keyed to a femoral trial component. Alternatively, the femoral drill guide may be keyed to the cuts which are made on the femur to receive the femoral component. In either case, the femoral drill guide is received and affixed relative the femur to allow for a substantially fixed guiding of the drill bit that produces the femoral tunnels. A plurality of femoral drill guides may also be provided to produce differing femoral tunnels 74. Again, the different femoral tunnels produce various and different constraints in the implanted knee prosthetic.

These and other similar instruments allow for a precise placement of the components during implantation. Moreover, a plurality of precisely formed components may be selected and used to form an optimum or selected knee geometry and range of motion. This allows a physician to selectively choose which of a plurality of sets of knee prosthesis are required for a particular patient. Each set may have specific constraint and rollback values depending upon the various tunnels which are formed by the femoral or tibial drill guides. Thus the tibial and femoral tunnels, formed to receive the ACL graft 70 or the PCL graft 90, are formed at the appropriate angles to produce the desired amount of constraint and rollback in the prosthetic knee.

Next, the tibial component 18 and the femoral component 16 are attached. The tibial component 18 is attached to the resected portion of the tibia 12 and oriented to allow the tibial bearing surface 54 to extend generally away from the proximal end portion of the tibia 12. The femoral component 16 is attached to the resected portion of the femur 14 to allow the bearing surfaces 28, 30 to extend generally distally from the end portion of the femur 14. The tibial component 18 and the femoral component 16 may be affixed with any generally known fixation means. For example, a bone cement may be used and the rough areas allow for bone ingrowth.

The next step is to install the bearing member 20 between the tibial component 18 and the femoral component 16. Although it will be understood that the tibial tunnel 72 and femoral tunnel 74 may be formed before the bearing 20 is installed. The bearing 20 is positioned to allow the first and second bearing surfaces 62, 64 to articulate with the femoral bearing surface 28, 30 and the bearing surface 60 to articulate with the tibial bearing surface 54. Essentially, the bearing 20 is positioned between the tibial component 18 and femoral component 16.

To connect the knee prosthetic 10, the ACL graft 70 is attached to the tibia 12, with the tibial fixation device 80, and the femur 14, with the femoral fixation device 76. In order to form the ACL graft 70, a biologic graft is prepared as is known in the art. The ACL graft 70 may be a transplant of several different types. For example, the ACL grafts 70 may be an allograft, xenograft, autograft, or synthetic graft. A synthetic graft may be any non-biological tissue that simulates substantially all biological features of an ACL graft 70. One specific example is the ACL graft 70 being formed from a hamstring autograft. In this manner, the patient provides the patient's own ACL graft 70.

As described above, the tibial tunnel or bore 72 is drilled through the tibia 12. This is generally performed using the tibial drill guide 92 attached to the tibial trial component 91. The femoral tunnel 74 is formed in the femur 14 also generally using a femoral drill guide. The tibial tunnel 72 will typically have a diameter between about 7 to 13 millimeters and is bored utilizing the drill bit 99 and a driver. The tibial tunnel 72 exits at the anterior tibial clearance 50 and enters the tibia 12 at about 50 millimeters from the tibial plateau medial to the tibial tubercle or at the medial cortex. Since the tibial tunnel 72 angles through the tibia 12, it creates an elliptical entrance opening 73 and an elliptical exit opening adjacent the anterior tibial clearance 50. As discussed above, appropriate femoral or tibial drill guides may be used to form the tunnels. Alternatively, one drill bit may form the corresponding tibial and femoral tunnels.

To secure the ACL graft 70, the femoral fixation device 76 is inserted into the femur 14. The femoral fixation device 76 may be any of a variety of fasteners operable to secure the ACL graft 70 to the femur 14. In a preferred embodiment, a bone mulch screw provides the femoral fixation device 76 in the femur 14. The femoral fixation device 76 includes a shaft portion 76a engaging a portion of the ACL graft 70 and a threaded portion 76b engaging the bone of the femur 14. The femoral fixation device 76 is installed by drilling the fixation tunnel 75 in the femur 14 and threading the femoral fixation device 76 into the femur 14.

The femoral fixation device 76, as it is inserted into the fixation tunnel 75, mulches or dislodges bone portions of the femur 14 to fill the fixation tunnel 75 with bone mulch. This provides a first initial fixation of the femoral fixation device 76 into the fixation tunnel 75 which is substantially permanent. Furthermore, the bone mulch created within the fixation tunnel 75 increases the speed of bone ingrowth into the fixation tunnel 75. As bone grows into the fixation tunnel 75, the femoral fixation device 76 is substantially permanently held in place such that it will not move out of the fixation tunnel 75. It will be understood, however, that the bone mulch screw is not the only method of affixing the ACL graft 70 within the femoral tunnel 74.

Once the knee prosthetic 10 has been implanted and the ACL graft 70 fixed in place using the femoral fixation device 76, the proper tension of the ACL graft 70 may be produced before the tibial fixation device 80 is placed. Common methods for tensioning the ACL graft 70 include those described U.S. Pat. No. 5,507,750 entitled "Method and Apparatus for Tensioning Grafts and Ligaments" which is incorporated herein by reference. After tensioning, the ACL graft 70 is secured to the tibia 12 with the tibial fixation device 80.

Figure 8:
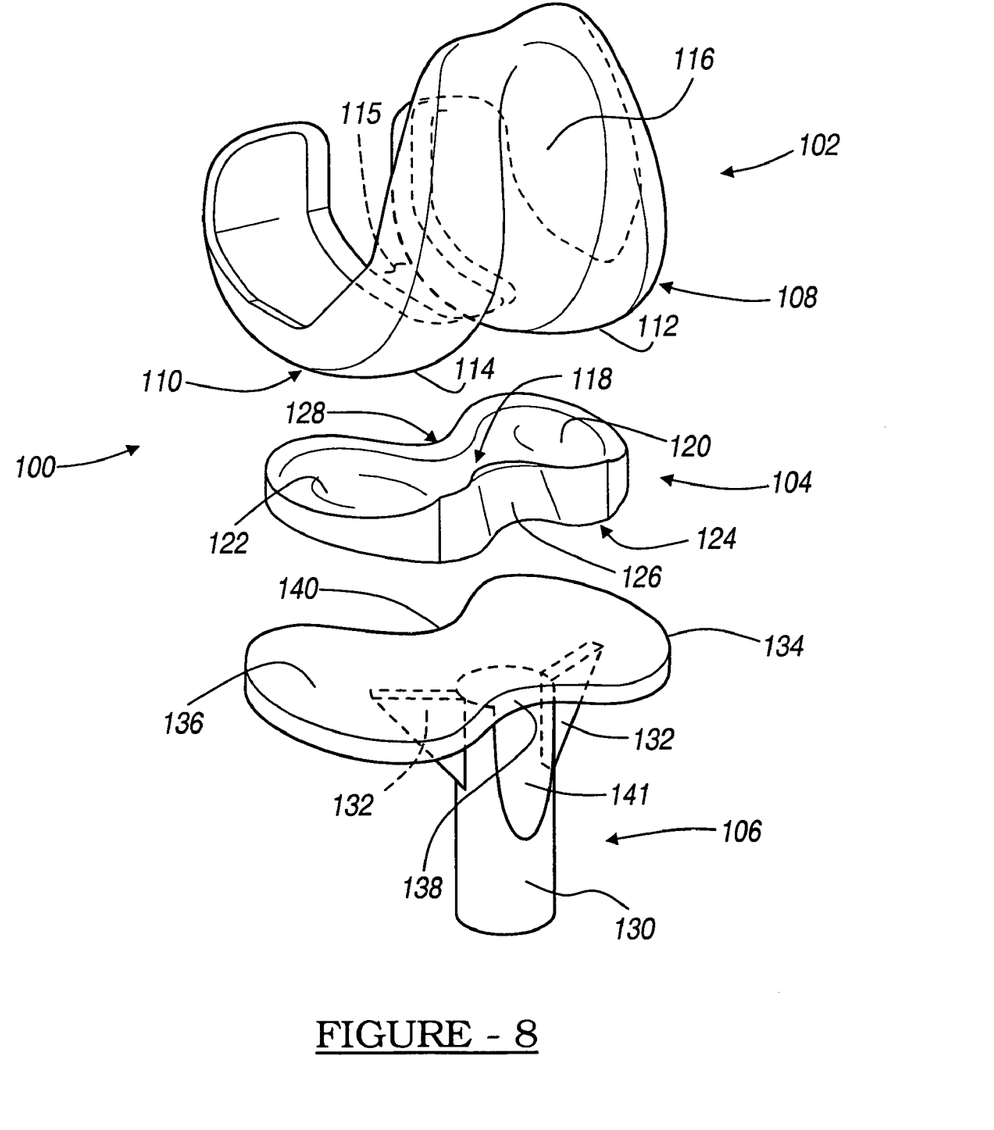
FIG. 8 is an exploded perspective view of a floating bearing knee prosthetic according to a second embodiment.
Figure 9:
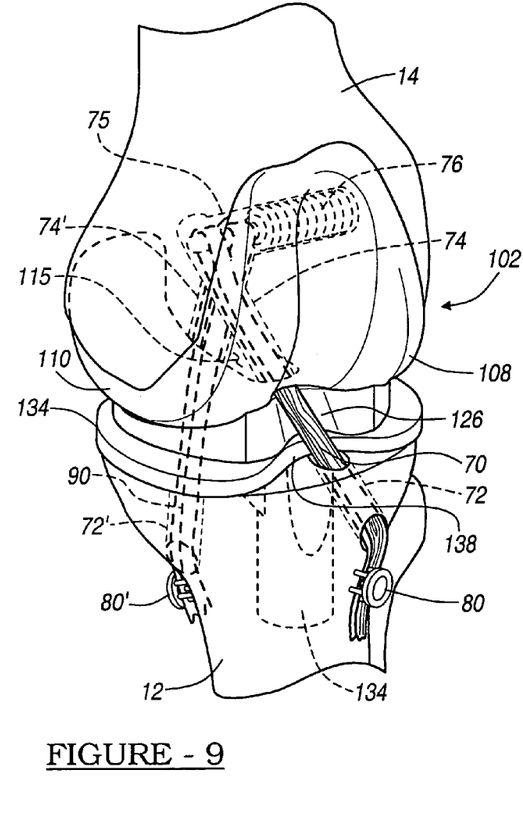
FIG. 9 is a perspective view of the knee prosthesis of FIG. 8 implanted and including both an ACL and a PCL graft.

With reference to FIGS. 8 and 9, a second embodiment of a knee prosthetic 100 is illustrated where like numerals identify like portions noted above. The knee prosthetic 100 includes a femoral component 102, a bearing 104, and a tibial component 106. The femoral component 102 includes a first condyle 108 and a second condyle 110. The first condyle 108 defines a first femoral bearing surface 112 and the second condyle 110 defines a second femoral bearing surface 114. A femoral clearance 115 is defined between the first condyle 108 and the second condyle 110. A patellar groove 116 is defined between the first condyle 108 and the second condyle 110. The patellar groove 116 may receive either a natural patella or an implant patella.

The bearing 104 is substantially a floating bearing. The bearing 104 includes a femoral bearing surface 118, which includes a first condyle bearing surface 120 and a second condyle bearing surface 122. The condyle bearing surfaces 120, 122 receive the bearing surfaces 112, 114 of the femoral component 102. The bearing 104 also includes a tibial bearing surface 124. Formed on the anterior side of the bearing 104 is a anterior bearing passage or clearance 126. Formed on a posterior side of the bearing 104 is a posterior bearing passage or clearance 128.

The tibial component 106 includes a tibial stem 130 which is formed to be received into a superior portion of the medial portion of the tibia 12. Stabilization wings 132 are included to both reinforce a tibial plateau 134 and to resist rotation of the tibial component 106 after implantation. The proximal end of the tibial plateau 134 defines a tibial bearing surface 136. The tibial bearing surface 136 is designed to substantially mate with the tibial bearing surface 124 of the bearing 104 after implantation. Also formed into an anterior edge of the tibial plateau 134 is an anterior tibial passage or clearance 138. Formed on a posterior edge of the tibial plateau 134 is a posterior tibial passage or clearance 140. The tibial stem 130 may also include a stem clearance 141 for the respective tibial clearances 138 and 140. The tibial stem 130 may also have an I-beam configuration as illustrated in the trial tibial steam 91a. The I-beam configuration includes inherent clearances so that an additional steam clearance 141 may not be required. It will also be understood that an I-beam configuration may be used for the stem 48 according to the above embodiments.

Generally, the bearing surfaces 112, 114 of the femoral component 102 and the tibial bearing surface 136 of the tibial component 106 are highly polished so that the bearing 104 is able to move freely between the bearing surfaces. The design of the knee prosthetic 100 is substantially similar to the knee prosthetic 10 of the first embodiment. That is, that the tibial stem 130 and the proximal sides of the femoral component 102 may be provided with any means for fixation into the respective bones. According to the knee prosthetic 100 rather than including a closed clearance, open clearances 126, 128, 138, and 140 are provided.

With particular reference to FIG. 9, the knee prosthetic 100 is implanted into a knee, and the ACL graft 70 or PCL graft 90 are used to reattach the tibia 12 and femur 14. The ACL graft 70 is able to clear the anterior tibial clearance 138 and the anterior bearing clearance 126. Rather than being enclosed within bores formed in the knee prosthetic 10, the knee prosthetic 100 allows more freedom of the ACL graft 70 after implantation. Similarly, the PCL graft 90 is allowed to clear the posterior tibial clearance 140 and the posterior bearing passage 128. Having open clearances rather than bores allows greater movement of the grafts 70 and 90 after implantation and more natural movement of the knee. Additionally, as the bearing 104 translates on the tibial bearing surface 136, as the knee goes into flexion, the ACL graft 70 is not impinged in any clearances because the anterior bearing clearance 126 is substantially open. Additionally, the posterior bearing clearance 128 will be great enough so that the PCL graft 90 does not become impinged by the bearing 104 as the bearing 104 articulates as the knee flexes.

The method of implanting the knee prosthetic 100 is substantially similar to implanting the knee prosthetic 10 of the first embodiment. Additionally, the implantation of the ACL graft 70 or the PCL graft 90 is substantially similar with the knee prosthetic 100, according to the second embodiment as is implantation with the knee prosthetic 10 according to the first embodiment. Therefore, the methods of implanting the knee prosthetic 100 and the associated ACL or PCL grafts 70 and 90 will not be repeated.

Figure 10A:
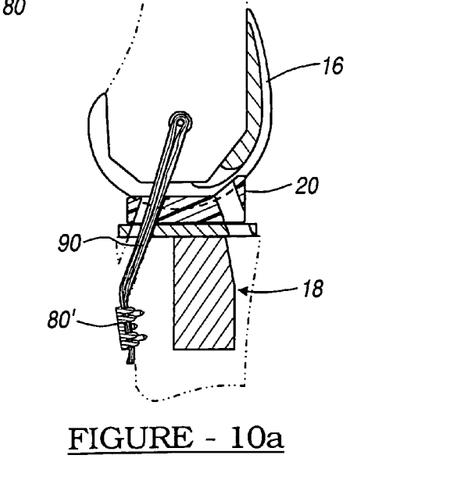
FIGS. 10a–10e are partial sagittal sectional views of the knee joint prosthesis shown in FIG. 8 and an ACL and PCL graft illustrating five different positions of the femoral component with respect to the tibial component during a range of flexion from full extension to full flexion.
Figure 10B:
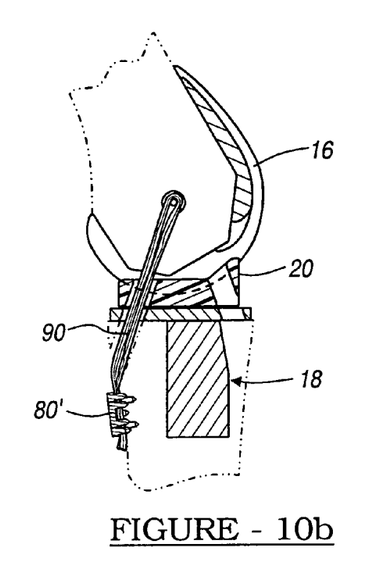
Figure 10C:
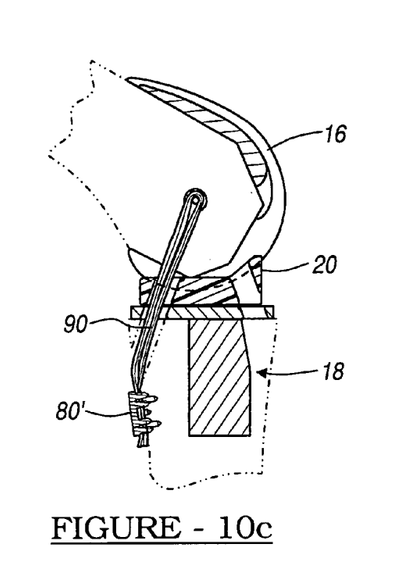
Figure 10D:
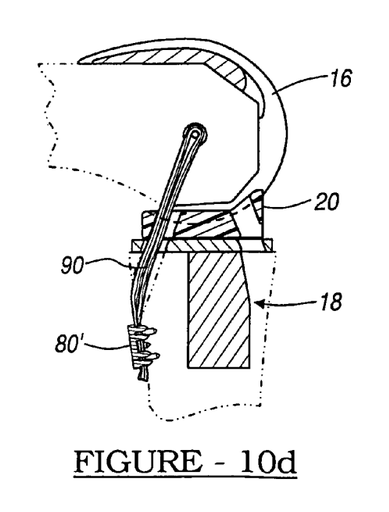
Figure 10E:
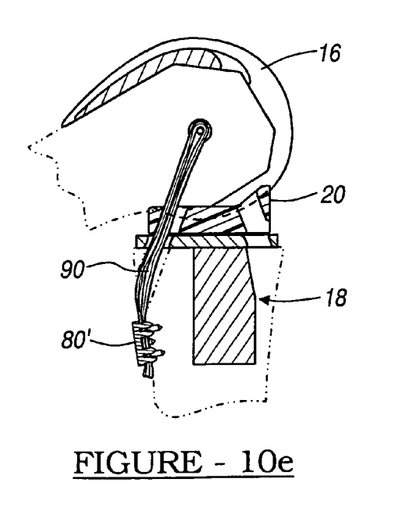

Turning to FIGS. 10a–10e, partial sagittal sectional views of the joint prosthetic 10, illustrating the movement of the femoral component 16, the floating bearing 20, and the PCL graft 90 relative to the tibial component 18, are shown from full extension in FIG. 10a to full flexion in FIG. 10e. Although the motion illustrated in relation to the first embodiment of the knee prosthetic 10, it will be understood the second embodiment of the knee prosthetic 100 works in a substantially similar manner. In FIG. 10a, the knee prosthetic 10, both anteriorly and posteriorly, is inherently stable at full extension when the patient is standing. In this position, the first and second femoral bearing surfaces 28 and 30 are rested within the first and second bearing surfaces 62 and 64 of the floating bearing 20, respectively. If the knee prosthetic 10 would undergo a large hyperextension or forward rollback forces (approximately 10 degrees), the PCL graft 90 would stabilize the femur 14 and the tibia 12. This engagement will also avoid posterior dislocation of the femoral component 16 relative to the tibial component 18.

The femoral component 16, with respect to the tibial component 18 and the floating bearing 20, is generally most unrestricted between full extension, as illustrated in FIG. 10a and the point of flexion where the PCL graft 90 begins to hold and stabilize the femur 14 and the tibia 12 generally, as illustrated in FIG. 10b. This stabilization generally occurs as the knee begins to flex. Within this range, the femoral component 16 is permitted to translate in the sagittal plane along with the bearing 20 relative to the tibial component 18. As the bearing 20 is allowed to float or articulate on the tibial bearing surface 46, the anterior bearing clearance 66 does not substantially interfere with the PCL graft 90. Simply, as the bearing 20 articulates on the tibial bearing surface 46, the bearing 20 does not impinge or force the dislocation of the PCL graft 90. Therefore, the anterior bearing clearance 66 is large enough or has dimensions great enough to allow movement of the bearing 20 while not impinging upon the PCL graft 90.

As the knee begins to flex, the bearing 20 does not articulate much. As the knee moves through flexion, however, as illustrated particularly in FIG. 10a, the bearing 20 moves posteriorly so that the PCL graft 90 is positioned closer to the anterior portion of the anterior bearing passage 66. As the knee goes into greater and complete flexion, as illustrated particularly in FIGS. 10d and 10e, the PCL graft 90 is substantially adjacent to the anterior portion of the bearing 20 as the bearing 20 moves posteriorly and the knee flexes.

The femoral component 16 and the floating bearing 20 are both able to move anteriorly and posteriorly relatively freely with respect to the tibial component 18, via the bearing surfaces between the floating bearing 20 and the tibial tray 46. It should be further understood that the exact amount of translation in the sagittal plane permitted by the knee prosthetic 10 will of course, vary depending on the forces imparted by local soft tissues, muscles, tendons, ligaments, as well as forces transmitted from the tibia 12 and femur 14. These forces will vary depending upon several factors such as differences from patient to patient and from activity to activity.

When flexion exceeds a certain degree, rollback of the floating bearing 20 posteriorly relative to the tibial tray 46 occurs. Rollback of the floating bearing 20 is caused when the PCL graft 90 engages both the tibia 12 and the femur 14 to prevent relative anterior-posterior translation therebetween. While this forced rollback of the bearing 20 is occurring, the first and second bearing surfaces 28, 30 are fully or nestingly received within the bearing surfaces 62, 64 of the floating bearing 20. This forced rollback of the bearing 20 creates the desired femoral rollback of an anatomical knee joint. As flexion continues from about 60 degrees shown in FIG. 10c to about 110 degrees shown in FIG. 10e, a forced rollback of the bearing 20 relative to the tibial tray 46 continues to occur, while a surface contact area between the first and second condyles 24 and 26 and the bearing 20 increases with flexion of the joint, via cooperating surfaces.

As can be observed from FIGS. 10a–10e, the forced rollback enables the surface contact area between the femoral component 16 and the bearing 20 to be increased during flexion of the knee prosthetic 10. This full surface contact is achieved because rollback is occurring between the bearing 20 and the tibial component 18, via a sliding of the bearing 20 posteriorly atop the tibial tray 46.

Figure 11:
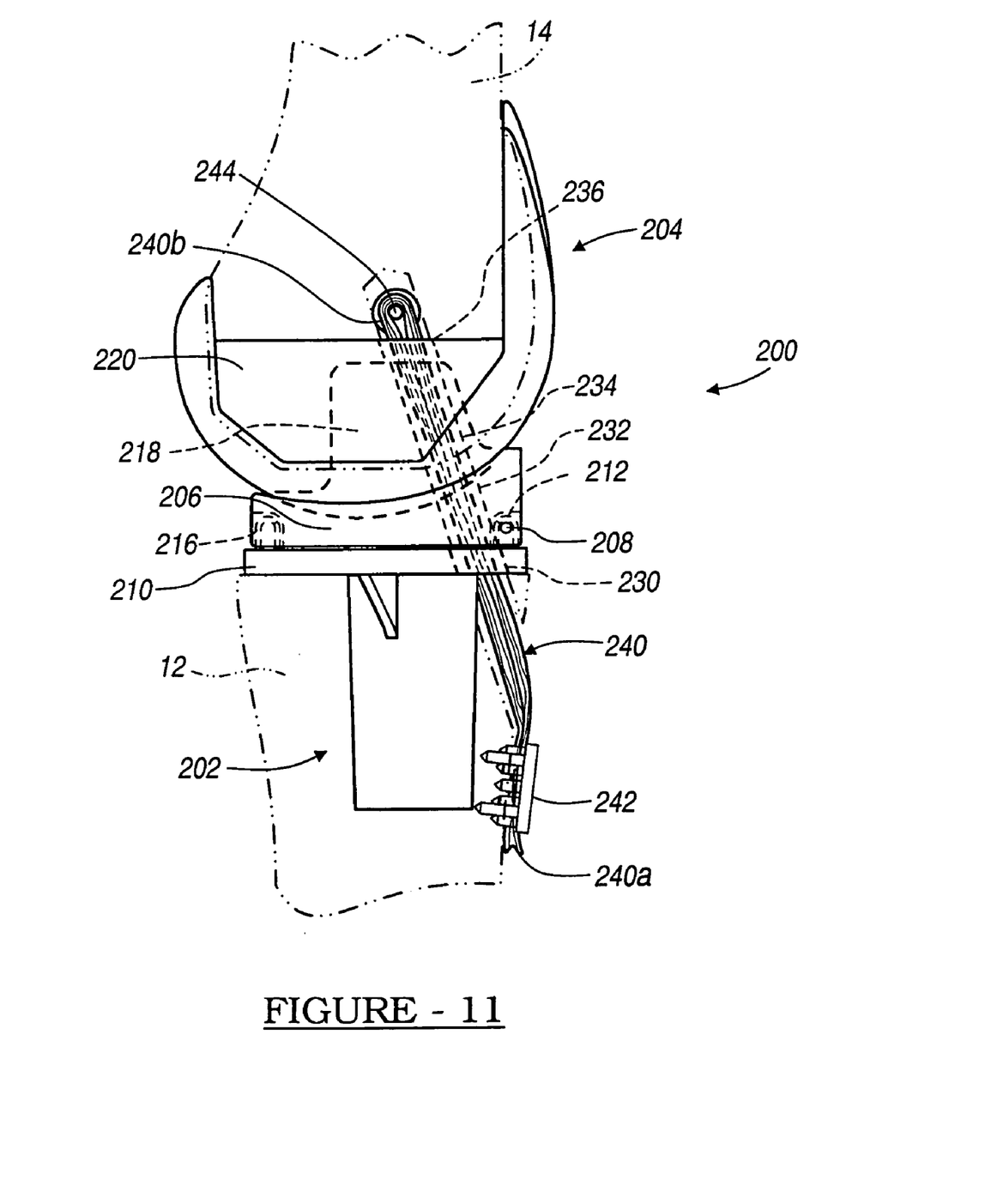
FIG. 11 is a sagittal elevational view of a fixed bearing knee prosthetic according to a third embodiment.

According to a third embodiment, and with reference to FIG. 11, a posterior stabilized (PS) fixed bearing knee prosthetic 200 is illustrated according to the third embodiment of the present invention. The knee prosthetic 200 replaces the articulating portions of the tibia 12 and the femur 14. Therefore, the knee prosthetic 200 includes a tibial component 202, a femoral component 204, a bearing member 206, and a first locking member or bar 208. The bearing 206 is locked to the tibial component 202 with the locking bar 208. It will be understood, however, that the bearing member 206 may be locked to the tibial component 202 through any appropriate means such as a screw or adhesive. The fixed bearing knee may be similar to known fixed bearing knees such as that disclosed in U.S. Pat. No. 5,330,534, entitled "Knee Joint Prosthesis With Interchangeable Components," incorporated herein by reference. These previously known fixed bearing knees, however, are required to be augmented according to the present invention as described herein.

Generally, the bearing member 206 is fixed to the tibial component through an interaction of the locking bar 208. The tibial component 202 includes a tibial plateau 210 from which extends anterior locking tabs 212. These anterior locking tabs 212 include fingers 214 which engage the bearing member 206. The tibial plateau 210 also includes a posterior locking tab 216. Generally, the bearing member 206 will first engage the posterior locking tab 216 and then is snapped over the anterior locking tabs 212. Once in place, the locking bar 208 is slid through the bearing member 206 and the locking tabs 212 so that a locking engagement is created between the bearing member 206 and the locking tabs 212. In this way, the bearing member 206 is held permanently in a single position relative to the tibial component 212. The articulating region of the PS fixed bearing knee prosthetic 200 is defined substantially by the same portions as the articulating region of the cruciate retaining floating bearing knee prosthetic 10, save that the posterior region is defined by the anterior surface of the bearing 208. Generally, this is because the bearing 208 is fixed to the tibial component 202.

The fixed bearing prosthetic 200 may also include a posterior stabilized feature. In particular, a posterior stabilized (PS) post 218 is included to engage an intercondylar box 220, formed between the condyles, of the femoral component 204. The PS post 218 may extend either from the tibial plateau 210 or from the bearing member 206. Regardless, as the femoral component 204 rides or articulates on the bearing member 206, the PS post 218 engages the box 220 to hold the femoral component 204 in a posterior stabilized position. In particular, this limits the range of motion of the femoral component 204 thereby limiting the range of motion of the femur 14 relative to tibia 12. It will be understood, that the femoral component 204 includes a first and second condyle and the bearing member 206 includes a first and second bearing surface to receive each condyle as described in the previous embodiments.

The tibial component 202 further includes an anterior tibial clearance or passage 230. The bearing member 206 also includes an anterior bearing clearance or passage 232. When the PS post 218 is present, it will also include an anterior clearance or passage 234. Also, an anterior box clearance or passage 236 is included in the box 220. Each of these anterior clearances 230, 232, 234, and 236 are provided to allow an ACL graft 240 to pass so that it may be affixed to an anterior portion of the tibia 12 and within an interior of the femur 14. A first graft portion 240a of the graft is affixed to the tibia 12 with a tibial fixation device 242 while a second graft portion 240b is affixed to the femur with a femoral fixation device 244. The tibial fixation device 242 and the femoral fixation device 244 are identical to the tibial fixation devices and femoral fixation devices described above. Again, it will be understood that any appropriate tibial fixation device and femoral fixation device may be used.

The knee prosthetic 200 according to the third embodiment does not allow the same knee kinematics as illustrated in FIGS. 10a–10e. Particularly, rather than replacing the posterior cruciate ligament with a PCL graft 90, a PS post 218 is included in the knee prosthetic 200. Therefore, the motion of the knee, generally created by the PCL, is here simulated with the PS post 218. Nevertheless, the ACL graft 240 has been implanted to replace the resected anterior cruciate ligament. Although the present invention allows for both the ACL and the PCL to be replaced with graft, this may not be possible due to a particular patients anatomy or ailments. Furthermore, it allows the physician a greater flexibility to be able to replace only one ligament while providing a mechanical constraint for other motions of the knee.

The prosthetics 10, 100, and 200 allow for a choice by a physician of performing a total knee replacement while also performing a reconstruction of the ACL and PCL ligaments. The total knee replacements according to the present invention provide means for a physician to reconstruct the ACL and PCL ligaments so the knee, after implantation, more closely mimics natural knee kinetics. Therefore the physician's abilities to perform knee implants is not limited by either resecting soft tissue and replacing it with an appropriate constricted knee, but allows the physician to perform reconstruction of the ACL and PCL ligaments while also performing a total knee replacement to replace the articulating regions of the femur and tibia.

Moreover, a plurality of specific knee replacements may be provided that provide a different amount of rollback or knee constraint in combination with a soft tissue replacement. As mentioned above, the natural knee is resected when performing a total knee replacement. After resecting the knee, a trial implant is used to determine the appropriate size and orientation of prosthetic for the femur and tibia for the implantation of the desired knee. The physician either pre- or intraoperatively may decide the best constraint and final geometry of the patient's knee, therefore allowing the physician to select the most appropriate knee implant. For example, different knee prosthetics may provide for the tibial and femoral tunnels to be formed at different angles. By providing this freedom to the physician, the most desirable knee may be chosen for the particular patient. Therefore, a physician will be able to determine what the appropriate amount of knee kinetics and freedom are required or tolerable for a particular patient. After such a decision is made, the physician may then choose the appropriate knee implant for that patient.

In addition, the components of the knee replacement can be particularly tuned or designed to allow different rollbacks and constraints. Therefore, during the implantation procedure, the specific tibial and femoral tunnels may be formed to work with the specific knee implants to provide the predetermined knee kinetics. As described above, during the trial phase of the procedure particular drill guides may be attached to the trial portions ensuring that the tibial and femoral tunnels are in the appropriate orientation to produce the predetermined actions of the reconstructed knee. Therefore, the physician will be able to produce in the patient the predetermined and best knee kinetics.

The floating bearing prosthetic 10 and 100 may be used when the patient has greater retention of other soft tissues which cannot or do not need to be replaced with grafts. Additionally, the floating bearing knee prosthetic 10 and 100 requires less restricted femoral component 16 and tibial components 18, which also reduces the amount of bone resection that must occur. Therefore, if a patient only has one or two soft tissue ligaments that must be replaced with grafts, a cruciate retaining floating bearing knee prosthetic 10 and 100 may be a better choice than other types of knee prosthetics. Additionally, if other soft tissues such as muscle are not damaged, further restriction is not required.

On the other hand, the PS fixed bearing knee prosthetic 200 can be used when the patient has greater damage to soft tissues which cannot be replaced. Although the ACL graft 240 can be used with the PS fixed bearing knee prosthetic 200, other soft tissue or muscle weakness may need to be compensated for thus requiring this more constrained knee. Therefore, using the PS fixed bearing knee prosthetic 200, can provide a better option for particular patients.

It will also be understood that various combinations of intermediates of a PS fixed bearing knee prosthetic 200 and a cruciate retaining floating bearing knee 10 and 100 can be used. The cruciate retaining floating bearing knee prosthetic 10 and 100 illustrates a knee prosthetic with minimal constraint. Whereas, the PS fixed bearing knee prosthetic 200 illustrates a greater amount of constraint. For example, the femoral component 16 of the first embodiment may be used with a tibial component which includes a fixed bearing but not a PS post. The bearing is fixed to the tibial component to reduce the freedom of motion of the knee, but still allows greater knee motion than that of the posterior stabilized knee. In addition, the femoral component 16 may allow for easier access to implant both the ACL graft 70 and the PCL graft 90. It will also be understood that other soft tissues, such as the medial, lateral, and collateral ligaments, may also be used in conjunction with the present invention. This will provide a surgeon with the greatest ability to complete a surgery such that a patient will be able to have the greatest range of motion, and that may most closely mimics a natural knee.

The prosthetic as described herein allows the surgeon to implant a knee prosthetic and a graft, which simulates the movement of a natural knee more closely. This allows a patient greater range of motion and more freedom after the knee prosthetic 10, 100, or 200 has been implanted. Therefore, rather than simply either replacing the articulating portions of the knee or replacing soft tissue portions of the knee, the two may now be performed at the same time that is, on the same knee, allowing the surgeon additional options to assist patients.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A knee joint prosthesis for replacing the articulating portion of a femur and a tibia and allowing for the replacement of soft tissue, comprising:
   a femoral component adapted to be secured to the distal end of the femur and having a femoral bearing surface;
   a tibial component adapted to be secured to the proximal end of the tibia and having a tibial surface;

a bearing member having a first bearing surface operable to articulate with the femoral bearing surface and a second surface to be positioned adjacent said tibial surface; and a graft interconnecting the femur to the tibia and intersecting a knee articulating region, said graft operable to control movement of the femoral component relative to the tibial component.

2. The knee joint prosthesis of claim 1, wherein said second surface is a bearing surface operable to articulate with said tibial surface.

3. The knee joint prosthesis of claim 1, wherein said graft may be connected to the femur in a plurality of locations, each location producing a unique knee joint prosthesis motion.

4. The knee joint prosthesis of claim 1, further comprising a second graft connecting the femur to the tibia, said second graft operable to control movement of the femoral component relative to the tibial component.

5. The knee joint prosthesis of claim 1, wherein said graft is a biological graft.

6. The knee joint prosthesis of claim 1, wherein said graft has a first end and a second end wherein said first end is affixed to the femur and said second end is affixed to the tibia.

7. A knee joint prosthesis for replacing the articulating portion of a femur and a tibia and allowing for the replacement of soft tissue, comprising:

a femoral component adapted to be secured to the distal end of the femur and having a femoral bearing surface;

a tibial component adapted to be secured to the proximal end of the tibia and having a tibial surface;

a bearing member having a first bearing surface operable to articulate with the femoral bearing surface and a second surface to be positioned adjacent said tibial surface; and a graft interconnecting the femur to the tibia and intersecting a knee articulating region, said craft operable to control movement of the femoral component relative to the tibial component;

wherein said femoral component defines a femoral clearance, said bearing member defines a bearing clearance and said tibial component defines a tibial clearance; and wherein said graft passes at least one of said clearances when connecting the femur and the tibia.

8. The knee joint prosthesis of claim 1, wherein the knee prosthetic is selected from a combination of a first group comprising cruciate retaining or posterior stabilized; and from a second group comprising floating bearing or fixed bearing.

9. The knee joint prosthetic of claim 1, wherein said second surface is fixed relative said tibial bearing surface.

10. The knee joint prosthesis of claim 9, wherein said bearing is mechanically affixed to said tibial component.

11. The knee joint prosthesis claim 2, wherein said bearing member defines an elongated bearing clearance;

wherein said graft passes said elongated bearing clearance when connecting the femur and the tibia; and wherein said elongated bearing clearance is operable to allow said bearing member to articulate relative said tibial component when said graft is connecting the tibia and the femur.

12. A knee joint prosthesis system for replacing a portion of a femur and a tibia, and a graft for interconnecting the femur and the tibia, comprising:

a femoral component defining a femoral clearance and adapted to be secured to the distal end of the femur, said femoral component having a first femoral bearing surface and a second femoral bearing surface;

a tibial component adapted to be secured to the proximal end of the tibia, said tibial component having a tibial bearing surface defining a tibial clearance;

a bearing member defining a bearing clearance and having a first bearing surface operable to articulate with said first femoral bearing surface, a second bearing surface operable to articulate with said second femoral bearing surface, and a third surface adapted to be positioned adjacent said tibial bearing surface; and wherein the graft is positioned to clear said tibial clearance and having a first portion connected to a portion of the femur and a second portion connected to a portion of the tibia.

13. The system of claim 12, further comprising:

a mechanical fastener which connects said first portion of said graft to the femur; and a mechanical fastener which connects said second end of said graft to the tibia.

14. The system of claim 12, wherein the knee prosthetic is selected from a combination of a first group comprising cruciate retaining or posterior stabilized, and from a second group comprising floating bearing or fixed bearing.

15. The system of claim 12, wherein said graft is selected from a group comprising an allograft, a xenograft, an autograft, or a synthetic graft.

16. The system of claim 12, wherein said femoral clearance, said tibial clearance, and said bearing clearance are selected to include a substantially open clearance, a substantially surrounded clearance, or both.

17. The system of claim 12, wherein said graft clears at least one of said clearances when said graft connects the tibia and the femur.

18. The system of claim 12, wherein said bearing clearance includes a bearing tunnel and said tibial clearance includes a bore.

19. The system of claim 12, wherein said third surface is operable to articulate with said tibial bearing surface, wherein said bearing clearance is operable to allow said bearing member to articulate when said graft is connected to the tibia and the femur.

20. The system of claim 12, wherein said third surface is fixed adjacent said tibial bearing surface.

21. The system of claim 12, wherein said femoral clearance includes an anterior cruciate femoral clearance, a posterior cruciate femoral clearance, or both;

wherein said tibial clearance includes an anterior cruciate tibial clearance, a posterior cruciate tibial clearance, or both; and wherein said bearing clearance includes an anterior cruciate bearing clearance, a posterior cruciate bearing clearance, or both.

22. A method of replacing an articulating knee portion of a femur and a tibia comprising:

resecting an end portion of the tibia;

resecting an end portion of the femur;

attaching a tibial prosthetic component corresponding to the resected end portion of the tibia, the tibial prosthetic component having a bearing surface;

attaching a femoral prosthetic component corresponding to the resected end portion of the femur, the femoral prosthetic component having a bearing surface;

installing a bearing member between the tibial prosthetic component and the femoral prosthetic component, the bearing member having a first surface operable to articulate with the femoral bearing surface;

preparing a graft to operably connect the tibia and the femur; and operably interconnecting the tibia and the femur with said graft, such that said graft intersects a knee articulating region.

23. A method of replacing an articulating knee portion of a femur and a tibia comprising:
resecting an end portion of the tibia;
resecting an end portion of the femur;
attaching a tibial prosthetic component corresponding to the resected end portion of the tibia, the tibial prosthetic component having a bearing surface;
attaching a femoral prosthetic component corresponding to the resected end portion of the femur, the femoral prosthetic component having a bearing surface;
installing a bearing member between the tibial prosthetic component and the femoral prosthetic component, the bearing member having a first surface operable to articulate with the femoral bearing surface:
preparing a graft to operably connect the tibia and the femur;
operably interconnecting the tibia and the femur with said graft, such that said graft intersects a knee articulating region;
wherein operably interconnecting the tibia and the femur further includes:
forming a recess in the femur;
forming a recess in the tibia;
placing a first portion of said graft in said femur recess; and
placing a second portion of said graft in said tibial recess.

24. The method of replacing the articulating knee portion of a femur and a tibia of claim 23, wherein operably interconnecting the tibia and the femur further includes positioning a third portion of said graft adjacent a clearance in at least one of the tibial prosthetic component, bearing component, or said femoral component.

25. The method of replacing the articulating knee portion of a femur and a tibia of claim 24, wherein said step of operably interconnecting the tibia further includes the steps of securing said first portion of said graft in said recess in the femur and securing said second portion of said graft to the tibia.

26. The method of replacing the articulating knee portion of a femur and a tibia of claim 22 wherein said step of installing a bearing member includes fixing a second surface of said bearing member relative said tibial prosthetic component.

27. The method of replacing the articulating knee of a femur and a tibia of claim 22, wherein said step of operably interconnecting the tibia and the femur with a graft includes:
forming a tibial tunnel;
forming a femoral tunnel;
placing a femoral fixation device in said femoral tunnel;
looping said graft over said femoral fixation device to fix said graft in said femoral tunnel;
pulling a portion of said graft through said tibial tunnel; and
fixing said portion of said graft to the tibia.

28. A method of replacing the articulating knee portion of a femur and a tibia comprising the steps of:
resecting an end portion of the tibia;
resecting an end portion of the femur;
attaching a tibial prosthetic component corresponding to the resected end portion of the tibia, the tibial prosthetic component defining a bearing surface and a tibial clearance;
attaching a femoral prosthetic component corresponding to the resected end portion of the femur, the femoral prosthetic component defining a bearing surface;

installing a bearing member between said tibial prosthetic component and said femoral prosthetic component, the bearing member defining a bearing clearance and having a first surface operable to articulate with the femoral bearing surface;
preparing a graft to operably connect the tibia and the femur; and
operably interconnecting the tibia and the femur and intersecting a knee articulating region with said graft.

29. The method of claim 28, further comprising;
forming a femoral tunnel in the femur;
forming a tibial tunnel in the tibia having a superior exit;
aligning said tibial clearance with said superior exit of said tibial tunnel; and
aligning said bearing clearance with said tibial clearance.

30. The method of claim 29, further comprising:
passing said graft through said tibial tunnel;
clearing said tibial clearance and said bearing clearance with said graft;
passing said graft though said femoral tunnel;
holding said graft in said femoral tunnel; and
fixing said graft to the tibia.

31. The method of claim 30, further comprising:
looping said graft in said femoral tunnel such that said graft both enters and exits said femoral tunnel;
clearing said tibial clearance and said bearing clearance; and
passing through said tibial tunnel.

32. A knee joint prosthesis for replacing the articulating portion of a femur and a tibia and allowing for the replacement of soft tissue, comprising:
a femoral component adapted to be secured to the distal end of the femur and having a femoral bearing surface;
a tibial component adapted to be secured to the proximal end of the tibia and having a tibial surface; and
a bearing member having a first bearing surface operable to articulate with the femoral bearing surface and a second surface to be positioned adjacent said tibial bearing surface;
wherein each of said femoral component, tibial component, and bearing member are adapted to allow a graft to connect the femur to the tibia and intersect a knee articulating region.

33. The knee joint prosthesis of claim 32, further comprising:
a graft having a first end affixed to the femur and a second end affixed to the tibia;
wherein said femoral component, said tibial component, and said bearing member each define a clearance to allow said graft to clear said femoral component, said tibial component, and said bearing member.

34. The system of claim 33, wherein said femoral clearance, said tibial clearance, and said bearing clearance are selected to include a substantially open clearance, a substantially surrounded clearance, or both.

35. The knee joint prosthesis of claim 32, further comprising:
a graft having a first end affixed to the femur and a second end affixed to the tibia, wherein said graft intersects said knee articulating region.

36. The knee joint prosthesis claim 1, wherein at least one of said femoral component defines a femoral clearance, said bearing member defines a bearing clearance, or said tibial component defines a tibial clearance; and
wherein said graft passes at least one of said clearances when connecting the femur and the tibia.

* * * * *